United States Patent [19]

Zigman et al.

[11] 4,226,868

[45] Oct. 7, 1980

[54] PROCESSES FOR INHIBITING THE GROWTH OF SEA URCHIN EGGS

[75] Inventors: Seymour Zigman; Paul B. Gilman, Jr., both of Rochester, N.Y.

[73] Assignee: Eastman Kodak Company, Rochester, N.Y.

[21] Appl. No.: 945,283

[22] Filed: Sep. 25, 1978

[51] Int. Cl.$^3$ ............................................. A01N 43/42
[52] U.S. Cl. .................................... 424/258; 424/250; 424/256; 424/270; 424/272; 424/274; 424/DIG. 9; 424/DIG. 12
[58] Field of Search ............... 424/250, 258, 270, 272, 424/256, 274, DIG. 9, DIG. 12; 542/471, 474, 475

[56] References Cited

U.S. PATENT DOCUMENTS 3,623,883  11/1971  Bannert et al. .................. 542/475 X
3,657,291  4/1972  Jarolim et al. ....................... 260/408

OTHER PUBLICATIONS

The Biological Bulletin, vol. 153, No. 2, pp. 451-452, Oct. 1977.
Annals of New York Academy of Sciences, vol. 50, pp. 108, 117-119 (1948-1949).
Experimental Chemotherapy, Schintzer et al., pp. 842-844, 905-906 (1963).
Banno et al., Yukugaku Kenkyu, vol. 25, pp. 722-733 (1953).
Banno, Kanko Shikiso, vol. 34, pp. 1-22 (1955).
Ingraham, J. of Bacteriology, vol. 26, pp. 573-598 (1933).
Biochemical & Biophysical Research Communications, vol. 72, No. 3, pp. 824-829 (1976).
Science, Apr. 30, 1976.
Scientific American, May 1976, Data Sheet.
Eastman Kodak Co. Annual Report for 1976, p. 23, Mar. 1977.

*Primary Examiner*—Leonard Schenkman
*Attorney, Agent, or Firm*—Joshua G. Levitt

[57] ABSTRACT

The growth of sea urchin eggs is inhibited with a composition comprising a methine dye having a reduction potential equal to or more negative than −1.0 volt which is capable of being absorbed by the eggs, and an inert liquid carrier.

8 Claims, No Drawings

PROCESSES FOR INHIBITING THE GROWTH OF SEA URCHIN EGGS

This invention relates to compositions and processes for inhibiting the growth of sea urchin eggs. In a particular aspect it relates to compositions for this purpose containing methine dyes.

Sea urchins (*Arbacia punctulata* and *Lytechinus variegatus*) are small ocean-dwelling animals having a shell bearing numerous movable spines. The eggs of sea urchins have been a favorite subject for biological and biochemical studies in the laboratory. Their relatively large size and the short time from fertilization of an egg to embryo development are among the factors favoring their use in model biological and biochemical studies. Since the natural habitat of sea urchins is in warm coastal waters they occasionally come in contact with humans bathing in the ocean, with painful consequences to the bathers.

We have found compositions and processes for inhibiting the growth of sea urchin eggs. These compositions and processes are useful for arresting the development of fertilized sea urchin eggs at a desired point during their growth so that they can be preserved at that stage of growth for future observation and study. The compositions and processes of this invention are also useful for inhibiting the development and growth of sea urchin eggs in their natural habitat, thereby reducing the population of sea urchins in locations where they may be harmful to humans. The compositions can, in addition, be used to inhibit the growth of single celled marine organisms.

The compositions of this invention comprise:
(a) a methine dye which
 (i) has a reduction potential ($E_R$) equal to or more negative than $-1.0$ volt and
 (ii) is capable of being absorbed by the cell(s) of sea urchin eggs and
(b) an inert liquid carrier.

Processes of this invention comprise contacting the sea urchin eggs with a composition as described above.

Methine dyes (also referred to as methylidyne dyes) comprise a methine chain (i.e., a chain of carbon atoms with alternating double and single bonds) terminated at each end with a hetero atom. The terminal hetero atoms are typically nitrogen or oxygen atoms in various combinations, and generally they are contained in or attached to an unsaturated cyclic nucleus. Typical methine dyes are cyanine dyes, merocyanine dyes and oxonol dyes.

These dyes have found wide use in photography and related arts where they are employed, inter alia, as spectral sensitizers. The dyes are used to extend the spectral response of silver halide and other photosensitive materials to regions of the spectrum where they do not have inherent or native sensitivity. Specific methine dyes have been used as anthelmintic and antifilarial agents and the efficacy of a number of methine dyes as bactericides has been investigated.

In connection with investigations of the way methine dyes function in photographic materials, a large amount of data have been generated on the reduction and oxidation potentials of methine dyes. These investigations have indicated that reduction and oxidation potentials influence the ability of methine dyes to spectrally sensitize silver halide and other light sensitive materials.

We have found that the reduction potential of a methine dye influences the ability of the dye to inhibit the growth of sea urchin eggs. Dyes which can effectively inhibit the growth of sea urchin eggs are characterized by a reduction potential equal to or more negative than $-1.0$ volt and by the ability to be absorbed by the cells of the eggs.

The ability of methine dyes to inhibit the growth of sea urchin eggs does not appear to be related to the size, bulk, or molecular weight of the dye, except to the extent that such factors may affect the ability of the of the dye to be absorbed by the cell. Nor is it affected by substituents on the dye, except to the extent that each substituents may affect the reduction potential of the dye. The oxidation potential of the dye does not correlate with its ability to inhibit growth.

Reduction potentials for numerous methine dyes are available in the literature, as are suitable techniques for measuring them. Since the technique by which reduction potential is measured can influence to some extent the value obtained, a preferred technique for measuring reduction potentials to determine if a given dye is suitable for use in accordance with this invention is the technique described in R. J. Cox, *Photographic Sensitivity*, Chapter 15, Academic Press, 1973. This technique involves measurement at 20° C., of an approximately $10^{-4}$ molar solution of the dye in an electrolyte, such as methanol which is 0.05 molar in lithium chloride, using a dropping mercury electrode. The potential values are reported by reference to a silver-silver chloride electrode in a saturated solution of potassium chloride at 20° C. Plus and minus signs are assigned to the potential values according to the IUPAC Stockholm Convention, 1953.

The ability of a given methine dye to be absorbed by the cells of sea urchin eggs can be determined readily by a simple test. This test involves bringing a solution of the dye in an appropriate solvent, e.g., methanol, into contact with the sea urchin eggs and observing, with the aid of a light microscope if necessary, whether or not the interior of the sea urchin eggs is colored by the dye. Those dyes which color the sea urchin eggs are absorbed into their cells.

Preferred methine dyes for use in this invention are cyanine dyes. Such dyes have the nitrogen hetero atom which terminates the methine chain in a heterocyclic nucleus. Typical nuclei are quinoline, pyridine, isoquinoline, 3H-indole, benz[E]-indole, oxazole, thiazole, selenazole, imidazole, benzoxazole, benzothiazole, benzoselenazole, benzimidazole, naphthothiazole, naphthoxazole, naphthoselenazole, pyrylium, and imidazolepyrizine. These nuclei are typically in the form of quaternary salts and are joined to one another by a methine chain containing an odd number of carbon atoms so that the nitrogen atoms are conjugated to one another (i.e., separated by alternating double and single bonds).

Preferred cyanine dyes are those having the structure:

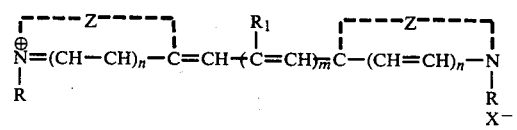

where:

each n is 0 or 1;
m is 0, 1, 2 or 3;
each Z represents the atoms to complete a heterocyclic ring system containing 1, 2, or 3 5- or 6-membered rings composed of atoms selected from carbon, nitrogen, oxygen, sulfur and selenium;
each R is hydrogen or alkyl of 1 to 4 carbon atoms;
$R_1$ is hydrogen or alkyl of 1 to 4 carbon atoms; and
$X^-$ is an anion.

The carrier with which the dye is associated can be any inert liquid which will aid introduction of the dye into the environment containing the sea urchin eggs. Since sea urchins and their eggs are normally found and maintained in sea water the carrier should be a material which is miscible with sea water and which will not interfere with dissolution of the dye in sea water. A preferred carrier is methanol.

The dye should be introduced into the environment of the sea urchin eggs in an amount sufficient to provide a final concentration which will inhibit cell growth. While the concentration effective to inhibit cell growth will vary depending upon the activity of the particular dye employed, useful concentrations are generally $10^{-6}$ to $10^{-4}$ molar.

The following examples further illustrate this invention.

In the examples which follow a number of methine dyes, varying in reduction potential, were evaluated for their ability to inhibit growth of sea urchin eggs. The dyes which were evaluated are listed below, by structure, in order of reduction potential ($E_R$).

| Dye | $E_R$ (volts) |
| --- | --- |
| 1 | −1.35 |
| 2 | −1.31 |
| 3 | −1.28 |
| 4 | −1.26 |
| 5 | −1.12 |
| 6 | −1.06 |
| 7 | −1.03 |
| 8 | −1.00 |

-continued

| Dye | $E_R$ (volts) |
|---|---|
| 9 (structure: bis-benzoxazole trimethine with NC substituents, N-CH₃, FSO₃⁻) | −0.99 |
| 10 (structure: bis-naphthothiazole trimethine, N-Et, PTS⁻) | −0.90 |
| 11 (structure: bis-benzothiazole trimethine, Cl substituents, N-Et, PTS⁻) | −0.86 |
| 12 (structure: bis-quinoxaline-imidazole trimethine, N-Allyl/N-Et, ClO₄⁻) | −0.81 |
| 13 (structure: bis-quinoxaline-imidazole trimethine, N-Et, Cl⁻) | −0.79 |
| 14 (structure: bis-chloroquinoxaline-imidazole trimethine, N-Ph, PTS⁻) | −0.65 |
| 15 (structure: bis-benzothiazole azamethine, N-Et, I⁻) | −0.64 |
| 16 (structure: bis-thiazoloquinoline trimethine, N-Et, Br⁻) | −0.63 |
| 17 (structure: bis-benzothiazole trimethine, NO₂ substituents, N-Et, Cl⁻) | −0.58 |
| 18 (structure: chloroquinoxaline-imidazole trimethine with diphenyl end, N-Allyl/N-Ph, PTS⁻) | −0.54 |

-continued

| Dye | | $E_R$ (volts) |
|---|---|---|
| 19 | 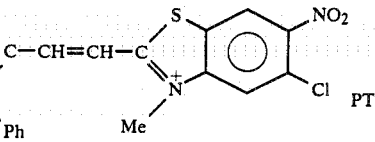 | −0.41 |
| 20 | 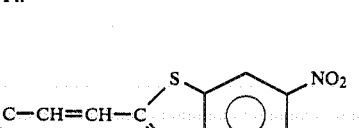 | −0.32 |
| 21 | 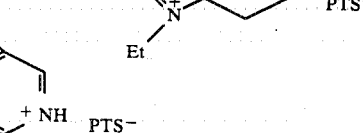 | −0.20 |
| 22 | 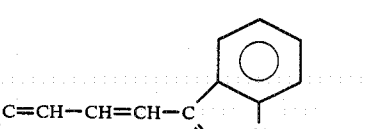 | −0.11 |

EXAMPLE 1

Effect of Reduction Potential and Absorption of Cell Division

To suspensions in filtered sea water of fertilized sea urchin eggs there were added, three minutes after fertilization, methanolic solutions of each of the dyes listed in Table I, below, in an amount sufficient to yield a final concentration of dye of between $10^{-5}$ and $10^{-6}$ molar. The final concentration of methanol was, at a maximum $1 \times 10^{-4}$ molar. The eggs were visually observed at 30 minutes and again at 60 minutes after fertilization using a light microscope. At 30 minutes after fertilization the ability of the dye to be absorbed by the eggs was determined and the formation of mitotic apparatus was noted. Absorption of dye is reported in Table I, below. With each of the dyes, the eggs produced a visible mitotic apparatus. At 60 minutes after fertilization cell division, or lack thereof, in the cells was observed. The ability of the cells to divide in the presence of dye is reported in Table I, below.

TABLE I

| Dye | $E_R$(volts) | Absorption | Cell Division |
|---|---|---|---|
| None | — | — | Yes |
| 1 | −1.35 | Yes | No |
| 2 | −1.31 | Yes | No |
| 3 | −1.28 | Yes | No |
| 4 | −1.26 | Yes | No |
| 5 | −1.12 | No | Yes |

TABLE I-continued

| Dye | $E_R$(volts) | Absorption | Cell Division |
|---|---|---|---|
| 6 | −1.06 | Yes | No |
| 7 | −1.03 | Yes | No |
| 8 | −1.00 | Yes | No |
| 9 | −0.99 | No | Yes |
| 10 | −0.90 | Yes | Yes |
| 11 | −0.86 | Yes | No |
| 12 | −0.81 | No | Yes |
| 13 | −0.79 | No | Yes |
| 14 | −0.65 | No | Yes |
| 15 | −0.64 | Yes | No |
| 16 | −0.63 | No | Yes |
| 17 | −0.58 | No | Yes |
| 18 | −0.54 | No | Yes |
| 19 | −0.41 | No | Yes |
| 20 | −0.32 | Yes | No |
| 21 | −0.20 | No | Yes |
| 22 | −0.11 | No | Yes |

From these results it will be observed that all dyes with reduction potentials equal to or more negative than −1.00 volt, which are absorbed by the eggs prevent cell division and hence inhibit growth. It will also be observed that the substantial majority of dyes which have reduction potentials less negative than −1.00 volt do not inhibit growth.

EXAMPLE 2

Effect of Dyes on DNA Synthesis

Example 1 was repeated except that there was added to the medium containing the eggs, prior to addition of dye, the radioactive compound 3H-thymidine at a concentration of 2.5 microcuries per milliliter. This compound is incorporated into cellular material, such as DNA, during growth. At 30 and 60 minutes after fertilization aliquots of the eggs were removed from the medium, thoroughly washed in sea water, homogenized in a glass homogenizer and the homogenate added to trichloroacetic acid to precipitate cellular material. The amount of radioactive material incorporated into the cells was determined by liquid scintillation measurements of the precipitated cellular material. The results are reported in Table II, below.

TABLE II

| Dye | $E_R$(volts) | Amount of 3H-Thymidine Incorporated (Counts Per Minute) | |
|---|---|---|---|
| | | 30 Min. | 60 Min. |
| None | — | 110 | 580 |
| 3 | −1.28 | 17 | 19 |
| 4 | −1.26 | 18 | 18 |
| 21 | −0.20 | 107 | 408 |

From this Table it will be observed that dyes with $E_R$ more negative than $-1.0$ volt inhibited incorporation of 3H-thymidine into egg cells whereas a dye with an $E_R$ less negative than $-1.00$ volt did not.

EXAMPLE 3

Effect of Dyes on Pre-Fertilized Eggs

The procedures of Examples 1 and 2 were repeated except that the dye was added to the medium containing the sea urchin eggs 10 minutes before fertilization and the eggs were examined as in Exmples 1 and 2 60 minutes after fertilization. Dye with $E_R$ more negative than $-1.00$ volt which were absorbed by the cells inhibited cell division and DNA synthesis. The results are reported in Table III, below.

TABLE III

| Dye | $E_R$(volts) | Absorption | Cell Division | Amount of 3H-Thymidine Incorporated (Counts per Minute) |
|---|---|---|---|---|
| None | — | — | Yes | 1400 |
| 1 | −1.35 | Yes | No | 150 |
| 4 | −1.26 | Yes | No | 380 |
| 5 | −1.12 | No | Yes | 1100 |
| 7 | −1.03 | Yes | No | 225 |

EXAMPLE 4

Effect of Dyes on Divided Eggs (Embryos)

Example 1 was repeated except that the eggs were allowed to divide to 8 and 16 cells (approximately 120 minutes after fertilization) before the dye was added. The eggs were observed 16 hours after addition of the dye to determine if further development to swimming embryos had occurred. Those dyes with $E_R$ equal to or more negative than $-1.00$ volt inhibited further development whereas dyes with $E_R$ less negative than $-1.00$ volt did not. The results are reported in Table IV, below.

TABLE IV

| Dye | $E_R$(volts) | Further Development |
|---|---|---|
| None | — | Yes |
| 1 | −1.35 | No |
| 2 | −1.31 | No |
| 3 | −1.28 | No |
| 8 | −1.00 | No |
| 9 | −0.99 | Yes |
| 17 | −0.58 | Yes |

This invention has been described in detail with particular reference to preferred embodiments thereof, but it will be understood that variations and modifications can be effected within the spirit and scope of the invention.

What is claimed is:

1. A process for inhibiting the growth of sea urchin eggs comprising contacting the eggs with a growth inhibiting concentration of a methine dye in an inert liquid carrier, the methine dye (i) having a reduction potential ($E_R$) equal to or more negative than $-1.0$ volt and (ii) being capable of being absorbed by the cells of sea urchin eggs.

2. A process of claim 1 wherein the final concentration of the dye in the environment of the eggs is $10^{-8}$ molar or greater.

3. A process of claim 2 wherein the final concentration is $10^{-6}$ to $10^{-4}$ molar.

4. A process of claim 1 wherein the methine dye is a cyanine dye.

5. A process of claim 4 wherein the cyanine dye has the structure:

$$\overset{\oplus}{\underset{R}{N}}=(CH-CH)_n-\overset{R_1}{\underset{}{C}}=CH-(C=CH)_{\overline{m}}C-(CH=CH)_n-\underset{R}{N} \quad X^{\ominus}$$

(with Z completing heterocyclic rings on each nitrogen)

where:
each n is 0 or 1;
m is 0, 1, 2 or 3;
each Z represents the atoms to complete a heterocyclic ring system containing 1, 2, or 3, 5- or 6-membered rings composed of atoms selected from carbon, nitrogen, oxygen, sulfur and selenium;
each R is hydrogen or alkyl of 1 to 4 carbon atoms;
$R_1$ is hydrogen or alkyl of 1 to 4 carbon atoms; and
$X^{\ominus}$ is an anion.

6. A process of claim 5 wherein the cyanine dye is selected from the group consisting of dyes having the structural formulae:

$$\underset{Ph}{\overset{S}{\diagup}}\underset{N}{\diagdown}C=CH-CH=CH-C\underset{\overset{+}{N}}{\overset{S}{\diagup}}\underset{Ph}{\diagdown} \quad I^-$$
$$\qquad \underset{Et}{\diagdown} \qquad \underset{Et}{\diagup}$$

-continued
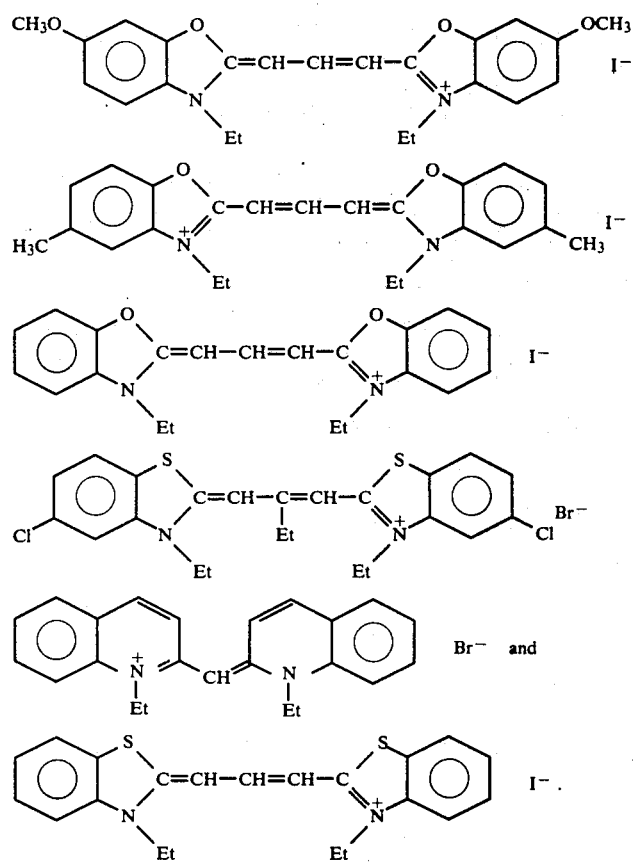
7. A process of claim 1 wherein the inert carrier is a solvent for the methine dye which is miscible in sea water.
8. A process of claim 7 wherein the inert carrier is methanol.